(12) United States Patent
Jaspart et al.

(10) Patent No.: US 10,660,903 B2
(45) Date of Patent: May 26, 2020

(54) ORODISPERSIBLE DOSAGE UNIT CONTAINING AN ESTETROL COMPONENT

(71) Applicant: ESTETRA SPRL, Liége (BE)

(72) Inventors: Séverine Francine Isabelle Jaspart, Bois-et-Borsu (BE); Johannes Jan Platteeuw, Boxtel (NL); Denny Johan Marijn Van Den Heuvel, Beuningen (NL)

(73) Assignee: ESTETRA SPRL, Liège (BE)

( * ) Notice: Subject to any disclaimer, the term of this patent is extended or adjusted under 35 U.S.C. 154(b) by 0 days.

(21) Appl. No.: 16/025,719

(22) Filed: Jul. 2, 2018

(65) Prior Publication Data

US 2019/0125759 A1   May 2, 2019

Related U.S. Application Data

(63) Continuation of application No. 15/185,337, filed on Jun. 17, 2016, now abandoned.

(30) Foreign Application Priority Data

Jun. 18, 2015 (EP) .................................. 15172747

(51) Int. Cl.
  *A61K 31/565* (2006.01)
  *A61K 9/00* (2006.01)
  *A61K 9/20* (2006.01)

(52) U.S. Cl.
  CPC ............ *A61K 31/565* (2013.01); *A61K 9/006* (2013.01); *A61K 9/0056* (2013.01); *A61K 9/2013* (2013.01); *A61K 9/2018* (2013.01); *A61K 9/2027* (2013.01); *A61K 9/2054* (2013.01); *A61K 9/2059* (2013.01); *A61K 9/2072* (2013.01); *A61K 9/2077* (2013.01); *A61K 9/2095* (2013.01)

(58) Field of Classification Search
  CPC .. A61K 31/565; A61K 9/0056; A61K 9/2054; A61K 9/2077; A61K 9/2095; A61K 9/006; A61K 9/2013; A61K 9/2018; A61K 9/2027; A61K 9/2059; A61K 9/2072
  See application file for complete search history.

(56) References Cited

U.S. PATENT DOCUMENTS

| | | | |
|---|---|---|---|
| 6,117,446 | A | 9/2000 | Place |
| 6,723,348 | B2 | 4/2004 | Faham et al. |
| 9,603,860 | B2 | 3/2017 | Perrin |
| 9,884,064 | B2 | 2/2018 | Platteeuw et al. |
| 9,987,287 | B2 | 6/2018 | Platteeuw et al. |
| 9,988,417 | B2 | 6/2018 | Ferreiro Gil et al. |
| 10,179,140 | B2 | 1/2019 | Perrin et al. |
| 2002/0132801 | A1 | 9/2002 | Heil et al. |
| 2004/0009960 | A1 | 1/2004 | Heil et al. |
| 2004/0198671 | A1 | 10/2004 | Bunschoten et al. |
| 2005/0070488 | A1 | 3/2005 | Coelingh Bennik et al. |
| 2005/0106240 | A1 | 5/2005 | Tanaka et al. |
| 2005/0147670 | A1 | 7/2005 | Hsu et al. |
| 2007/0048369 | A1 | 3/2007 | Foreman et al. |
| 2007/0286819 | A1 | 12/2007 | Devries et al. |
| 2007/0286829 | A1 | 12/2007 | Batista |
| 2008/0113953 | A1 | 5/2008 | Devries |
| 2010/0093679 | A1 | 4/2010 | Heil |
| 2011/0250274 | A1 | 10/2011 | Shaked |
| 2012/0077888 | A1 | 3/2012 | Ramtoola et al. |
| 2012/0220556 | A1 | 8/2012 | Heil |
| 2015/0045300 | A1 | 2/2015 | Ahuja et al. |
| 2015/0182540 | A1 | 7/2015 | Heil et al. |
| 2016/0310506 | A1* | 10/2016 | Platteeuw ............ A61K 9/0056 |
| 2016/0367567 | A1 | 12/2016 | Jaspart et al. |
| 2017/0216318 | A1 | 8/2017 | Perrin et al. |
| 2018/0153801 | A1 | 6/2018 | Jaspart et al. |
| 2018/0169022 | A1 | 6/2018 | Jaspart et al. |
| 2018/0185271 | A1 | 7/2018 | Jaspart et al. |

FOREIGN PATENT DOCUMENTS

| | | |
|---|---|---|
| CL | 200501207 | 1/2006 |
| CL | 201400802 | 11/2014 |
| CN | 1197387 A | 10/1998 |
| CN | 101443015 A | 5/2009 |
| CN | 101541326 A | 9/2009 |
| CN | 101631536 A | 1/2010 |

(Continued)

OTHER PUBLICATIONS

Coelingh Bennink et al., "Ovulation inhibition by estetrol in an in vivo model" Contraception, 2008, vol. 77, pp. 186-190.
International Search Report issued in International Patent Application No. PCT/EP2014/077127, dated Feb. 3, 2015.
Gardouh et al., "Preparation and Characterization of Mucoadhesive Buccal Film for Delivery of Meloxicam," (Jun. 2013) British Journal of Pharmaceutical Research, vol. 3, No. 4, pp. 743-766.
Haque et al., "Development of polymer-bound fast-dissolving metformin buccal film with disintegrants," (Oct. 2015) International Journal of Nanomedicine, vol. 10, Suppl. I: Challenges in biomaterials research, pp. 199-205.
U.S. Office Action dated Jul. 3, 2017 in U.S. Appl. No. 15/185,337 (US 2016-0367567 A1).
U.S. Office Action dated Jan. 3, 2018 in U.S. Appl. No. 15/185,337 (US 2016-0367567 A1).

(Continued)

*Primary Examiner* — Michael B. Pallay
(74) *Attorney, Agent, or Firm* — Foley & Lardner LLP (57) ABSTRACT

An orodispersible solid pharmaceutical dosage unit having a weight between 30 and 1,000 mg is disclosed. The dosage unit comprises (a) 0.1-25 wt. % of estetrol particles containing at least 80 wt. % of an estetrol component selected from estetrol, estetrol esters and combinations thereof; and (b) 75-99.9 wt. % of one or more pharmaceutically acceptable excipients. The solid dosage unit comprises at least 100 µg of the estetrol component and can be obtained by a process that comprises compressing a dry blend of estetrol particles and one or more pharmaceutically acceptable excipients into a solid dosage unit. The solid dosage unit is easy to manufacture and suited for sublingual, buccal or sublabial administration.

14 Claims, 1 Drawing Sheet

(56) References Cited

FOREIGN PATENT DOCUMENTS

| | | |
|---|---|---|
| CN | 102058604 A | 5/2011 |
| EP | 0 371 466 A1 | 6/1990 |
| EP | 20010201896 | 11/2002 |
| EP | 3046928 B1 | 7/2016 |
| EP | 3106148 A1 | 12/2016 |
| JP | 2005-523283 A | 8/2005 |
| JP | 2010-513514 A | 4/2010 |
| WO | WO-95/17895 | 7/1995 |
| WO | WO-0042955 A1 | 7/2000 |
| WO | WO 02/094275 A1 | 11/2002 |
| WO | WO 02/094276 A1 | 11/2002 |
| WO | WO 02/094278 A1 | 11/2002 |
| WO | WO 02/094279 A1 | 11/2002 |
| WO | WO 03/018026 A1 | 3/2003 |
| WO | WO-030180264 A1 | 3/2003 |
| WO | WO 03/041718 A1 | 5/2003 |
| WO | WO-2004006936 | 1/2004 |
| WO | WO-2004/019954 | 3/2004 |
| WO | WO-2004/041289 | 5/2004 |
| WO | WO-2004103377 | 12/2004 |
| WO | WO-2005/030175 | 4/2005 |
| WO | WO-2005/030176 | 4/2005 |
| WO | WO-2005/051400 | 7/2005 |
| WO | WO-2005/105103 | 11/2005 |
| WO | WO-2005115349 | 12/2005 |
| WO | WO-2005115351 | 12/2005 |
| WO | WO-2006120035 | 11/2006 |
| WO | WO 2007/081206 | 7/2007 |
| WO | WO-2007/106264 | 9/2007 |
| WO | WO-2008/003363 | 1/2008 |
| WO | WO-2008/003432 | 1/2008 |
| WO | WO 2008/156365 | 12/2008 |
| WO | WO 2010/033832 A2 | 3/2010 |
| WO | WO-2010089078 A1 | 8/2010 |
| WO | WO-2010/149273 | 12/2010 |
| WO | WO-2011/128336 | 10/2011 |
| WO | WO-2012/000981 | 1/2012 |
| WO | WO-2012/055840 | 5/2012 |
| WO | WO-2013012326 A1 | 1/2013 |
| WO | WO-2013021025 | 2/2013 |
| WO | WO-2013/090117 | 6/2013 |
| WO | WO 2014/159377 A1 | 10/2014 |
| WO | WO-2014/189836 | 11/2014 |
| WO | WO-2015/040051 | 3/2015 |
| WO | WO-2015086643 | 6/2015 |
| WO | WO-2016/053946 | 4/2016 |
| WO | WO-2016/187269 | 11/2016 |
| WO | WO-2016/203011 | 12/2016 |
| WO | WO 2016/207298 | 12/2016 |
| WO | WO-2016203006 | 12/2016 |
| WO | WO-2016203009 | 12/2016 |
| WO | WO-2016203044 | 12/2016 |
| WO | WO-2018/024912 | 2/2018 |
| WO | WO-2018/065076 | 4/2018 |

OTHER PUBLICATIONS

U.S. Office Action (Advisory Action) dated Apr. 13, 2018 in U.S. Appl. No. 15/185,337 (US 2016-0367567 A1).

Bianchi, Marcel, "Estetrol: Desde Un Estrogeno Fetal Hasta El Tratamiento De La Menopausia," Rev. Chil. Obstet. Ginceol 2009, 74(2) 123-26.

Luo Lianmei et al., Major research advances in estetrol. J Reprod Med, vol. 18(3), pp. 305-308, Dec. 31, 2009.

Savjani et al, "Drug solubility: importance and enhancement techniques", ISRN Pharm., 2012: 195727, Jul. 5, 2012.

Williams et al., Strategies to address low drug solubility in discovery and development, Pharmacological Reviews, vol. 65(1), pp. 416-445, Jan. 1, 2013.

Anderson et al., Effects of conjugated equine estrogen in postmenopausal women with hysterectomy: the Women's Health Initiative randomized controlled trial, JAMA, vol. 291(14), pp. 1701-1712, Apr. 1, 2004.

Archer et al., A randomized, double-blind, placebo-controlled study of the lowest effective dose of drospirenone with 17β-estradiol for moderate to severe vasomotor symptoms in postmenopausal women, Menopause, vol. 21(3), pp. 227-235, Mar. 1, 2014.

Bjarnason et al., Acute and long-term estradiol kinetics in smoking postmenopausal women, Climacteric, vol. 15(5), pp. 449-454, Oct. 1, 2012.

Bosworth et al., Depressive symptoms, menopausal status, and climacteric symptoms in women at midlife, Psychosom Med., 63(4):603-8, Jul.-Aug. 2001.

Coelingh Bennink Herjan J T et al, Clinical effects of the fetal estrogen estetrol in a multiple-rising-dose study in postmenopausal women, Maturitas, Elsevier, Amsterdam, NL vol. 91, pp. 93-100, XP029649879, Jun. 23, 2016.

Harlow et al., Executive summary of the Stages of Reproductive Aging Workshop + 10: addressing the unfinished agenda of staging reproductive aging, Menopause, vol. 19(4), Apr. 1, 2012.

Heinemann et al., International versions of the Menopause Rating Scale (MRS), Health Qual Life Outcomes, pp. 1:28, Jul. 30, 2003.

Heinemann et al., The Menopause Rating Scale (MRS) scale: A methodological review, Health Qual Life Outcomes, pp. 2:45, Sep. 2, 2004.

Heinemann et al., The Menopause Rating Scale (MRS) as outcome measure for hormone treatment? A validation study, Health Qual Life Outcomes, pp. 2:67, Oct. 22, 2004.

Hilditch et al., A menopause specific quality of life questionnaire: development and psychometric properties, Maturitas, vol. 24(3), pp. 161-175, Jul. 1, 1996.

Notelovitz et al., Initial 17β-Estradiol Dose for Treating Vasomotor Symptoms, Obstetrics and Gynaecology, vol. 95(5), pp. 726-731, May 1, 2000.

Portman et al., Genitourinary syndrome of menopause: new terminology for vulvovaginal atrophy from the International Society for the Study of Women's Sexual Health and the North American Menopause Society, Menopause, vol. 21(10), pp. 1063-1068, Oct. 1, 2014.

Rodstrom et al., a longitudinal study of the treatment of 25 hot flushes: the population study of women in Gothenburg during a quarter of a century, Menopause, vol. 9(3), pp. 156-161, May-Jun. 2002.

Santoro, Symptoms of menopause: hot flushes, Clin Obstet Gynecol, vol. 51(3), pp. 539-548, Sep. 1, 2008.

Simon et al., Menopausal hormone therapy for vasomotor symptoms: balancing the risks and benefits with ultra-low doses of estrogen, Expert Opin Investig Drugs, vol. 16(12), pp. 2005-2020, Dec. 1, 2007.

Utian et al., Comparative controlled trial of a novel oral estrogen therapy, estradiol acetate, for relief of menopause symptoms, Menopause, vol. 12(6), pp. 708-715, Oct. 8, 2005.

Visser and Bennink, Clinical applications for estetrol, Journal of Steroid Biochemistry and Molecular Biology 114, pp. 85-89, 2009.

Bennink et al., Pharmacokinetics of the fetal estrogen estetrol in a multiple-rising-dose study in postmenopausal women, Climacteric. 20(3), pp. 285-289, Mar. 7, 2017.

Bennink et al., Pharmacodynamic effects of the fetal estrogen estetrol in postmenopausal women: results from a multiple-rising-dose study, Menopause 24(6), pp. 677-685, Jun. 1, 2017.

Dinger et al., *Effectiveness of Oral Contraceptive Pills in a Large U.S. Cohort Comparing Progestogen and Regimen*, Obstet. & Gynecol., 117(1):33-40, Jan. 1, 2011.

Dinger et al., *Oral Contraceptive Effectiveness According to Body Mass Index, Weight, Age, and Other Factors*, Am. J. Obstet. Gynecol., 201:263e1-9, Sep. 1, 2009.

Duijkers et al., *A randomized study comparing the effect on Ovarian activity of a progestogen-only pill (Pop) containing desogestrel and a new Pop containing drospirenone in a 24/4 regimen*, Euro. J. Contracept. & Repro. Health Care, 20(6):419-27, Jun. 15, 2015.

Eiger et al., *Conception and pharmacodynamics profile of drospirenone*, Steriods, 68(10):891-905, Nov. 1, 2003.

Rosenbaum et al., *Inhibition of ovulation by a novel progestogen (drospirenone) alone or in combination with ethinylestradiol*, Euro. J. Contracept. & Repro. Health Care, 5(1):14-24, Mar. 1, 2000.

(56) References Cited

OTHER PUBLICATIONS

Al-Jefout et al., "Continuous Norethisterone Acetate versus Cyclical Drospirenone 3 mg/Ethinyl Estradiol 20 ug for the Management of Primary Dysmenorrhea in Young Adult Women," Journal of Pediatric and Adolescent Gynecology, vol. 29, No. 2, pp. 143-147, XP029421056, Sep. 3, 2015.
Andersch and Milsom: "An epidemiologic study of young women with dysmenorrhea", Am J Obstet Gynecol, 144(6), p. 655-660, Nov. 15, 1982.
Apter et al: "Bleeding pattern and cycle control with estetrol-containing combined oral contraceptives: results from a phase II, randomised, dose-finding study (FIESTA)", Contraception, 94(4), p366-373, Oct. 2016.
Arnal et al., "Tissue specificity of the membrane vs nuclear actions of estrogen receptor alpha: insights from targeted mutations in mouse models," Archives of Cardiovascular Diseases Supplements, (Apr. 2016) vol. 8(3), p. 217, Abstract 0333, Apr. 1, 2016.
Bagot et al: "The effect of estrone on thrombin generation may explain the different thrombotic risk between oral and transdermal hormone replacement therapy", J Thromb Haemost., 8(8):1736-1744, Aug. 1, 2010.
Bennink et al., "Estetrol review: profile and potential clinical applications," Climacteric vol. 11, Suppl. 1, pp. 7-58, XP009194877, Jul. 3, 2009.
Callejo et al: "Effect of a low-dose oral contraceptive containing 20 microg ethinylestradiol and 150 microg desogestrel on dysmenorrhea", Contraception, 68(3), p. 183-188, Sep. 1, 2003.
Dahlback et al: "Familial thrombophilia due to a previously unrecognized mechanism characterized by poor anticoagulant response to activated protein C: prediction of a cofactor to activated protein C", Proc Natl Acad Sci U S A., 90(3), p. 1004-1008, Feb. 1, 1993.
Davis et al: "Oral contraceptives for dysmenorrhea in adolescent girls: a randomized trial", Obstet Gynaecol, 106(1): 97-104, Jul. 1, 2005.
De Bastos et al: "Combined oral contraceptives: venous thrombosis", Cochrane Database Syst Rev, (3):CD010813, Mar. 3, 2014.
Duijkers et al: "Inhibition of ovulation by administration of estetrol in combination with drospirenone or levonorgestrel: Results of a phase II dose-finding pilot study", Eur J Contracept Reprod Health Care,.20(6), p. 476-489, Aug. 20, 2015.
Endrikat et al: "A twelve-month comparative clinical investigation of two low-dose oral contraceptives containing 20 micrograms ethinylestradiol/75 micrograms gestodene and 20 micrograms ethinylestradiol/150 micrograms desogestrel, with respect to efficacy, cycle control and tolerance", Contraception, 52(4), p. 229-235, Oct. 1, 1995.
Foidart, "Estelle®, Estetrol and drospirenone in oral contraception: E4 Freedom TM Phase 3 clinical study design," Presented at Eur. Soc. Contraception & Reprod. Health, 14th Cong, 2nd Global Conf., May 7, 2016.
Foidart, "Estetrol, the first human, physiological Selective Estrogen Receptor Modulator," Presented at Eur. Soc. Contraception & Reprod. Health, 14th Cong, 2nd Global Conf., May 8, 2016.
French: "Dysmenorrhea", Am Fam Physician, 71(2): 285-291, Jan. 15, 2005.
Harel., "Dysmenorrhea in adolescents and young adults: an update on pharmacological treatments and management strategies," Expert Opinion on Pharmacotherapy, vol. 13 No. 15, pp. 2157-2170, XP055389783, Sep. 18, 2012.
Harrington et al: "Cross-sectional association of endogenous steroid hormone, sex hormone-binding globulin, and precursor steroid levels with hemostatic factor levels in postmenopausal women", J Thromb Haemost., 15(1), p. 80-90, Jan. 1, 2017.
Hendrix and Alexander: "Primary dysmenorrhea treatment with a desogestrel-containing low-dose oral contraceptive", 66(6), p. 393-399, Dec. 1, 2002.
Kluft Cornelis et al: "Reduced hemostatic effects with drospirenone-based oral contraceptives containing estetrol vs ethinyl estradiol", Contraception, vol. 95, n°2, p. 140-147, Sep. 1, 2016.
Kluft, "Effects on estrogenic and haemostatic variables of estetrol in combination with drospirenone," Presented at Eur. Soc. Contraception & Reprod. Health, 14th Cong, 2nd Global Conf., May 5, 2016.
Mawet et al: "Unique effects on hepatic function, lipid metabolism, bone and growth endocrine parameters of estetrol in combined oral contraceptives", Eur J Contracept Reprod Health Care, 20(6), p. 463-475, Jul. 27, 2015.
Odlind et al: "Can changes in sex hormone binding globulin predict the risk of venous thromboembolism with combined oral contraceptive pills?", Acta Obstet. Gynecol. Scand., 81(6), p. 482-490, Jun. 1, 2002.
Proctor and Farquhar: "Dysmenorrhoea", BMJ Clin Evid, 9, pii: 0813, Mar. 1, 2007.
Rosing et al: "Oral contraceptives and venous thrombosis: different sensitivities to activated protein C in women using second- and third-generation oral contraceptives", Br J Haematol., 97(1), p. 233-238, Apr. 1, 1997.
Shulman "Estelle®, Estetrol: changing hormones in advancing oral contraception," Presented at Eur. Soc. Contraception & Reprod. Health, 14th Cong, 2nd Global Conf., May 6, 2016.
Strowitzki et al., "Efficacy of ethinylestradiol 20 μg/drospirenone 3 mg in a flexible extended reimen in women with moderate-to-severe primlary dysmenorrhea: an open-label, multicenter, ramdomised, controlled study," J. Fam. Plann. Reprod. Health Care (2012) vol. 38, pp. 94-101, Mar. 27, 2012.
Sundell et al, "Factors influencing the prevalence and severity of dysmenorrhoea in young women.", Br J Obstet Gynaecol, 97(7), p. 588-594, Jul. 1, 1990.
Tchaicovski and Rosing: "Mechanisms of estrogen-induced venous thromboembolism", Thromb Res., 126(1):5-11, Feb. 16, 2010.
Winkler et al: "Cycle control, quality of life and acne with two low-dose oral contraceptives containing 20 microg ethinylestradiol", Contraception, 96(6), p. 469-476, Jun. 1, 2004.
Wong et al: "Oral contraceptive pill as treatment for pirmary dysmenorrhoea", Cochrane Database Syst Rev., CD002120, Apr. 15, 2009.
Ylikorkala and Dawood: "New concepts in dysmenorrhea", Am J Obstet Gynecol, 130(7), p. 833-847, Apr. 1, 1978.
Zhang and Wan Po: Efficacy of minor analgesics in primary dysmenorrhoea: a systematic review, Jul. 1, 1998.
Anderson and Spencer: "Risk factors for venous thromboembolism", Circulation, 107, I-9-I-16, Dec. 1, 2003.
Dinger et al: "Risk of venous thromboembolism and the use of dienogest- and drospirenone-containing oral contraceptives: results from a German case-control study", J Fam Plann Reprod Health Care, 36(3):123-129, Jul. 1, 2010.
Jick et al: "Risk of idiopathic cardiovascular death and nonfatal venous thromboembolism in women using oral contraceptives with differing progestagen components", Lancet, 346(8990): p. 1589-1593, Dec. 16, 1995.
Lidegaard et al: "Hormonal contraception and risk of venous trhomboembolism: national follow-study", BMJ, 339:b2890, Aug. 13, 2009.
Lidegaard et al: "Risk of venous thromboembolism from use of oral contraceptives containing different progestogens and oestrogen doses: Danish cohort study, Aug. 2001", BMJ, 343:d6423, Oct. 25, 2011.
Poort et al: "A common genetic variation in the 3'-untranslated region of the prothrombin gene is associated with elevated plasma prothrombin levels and an increase in venous thrombosis", Blood, 88(10), p. 3698-3703, Nov. 15, 1996.
Sidney et al: "Recent combined hormonal contraceptives (CHCs) and the risk of thromboembolism and other cardiovascular events in new users", Contraception, 87(1), p. 93-100, Jan. 1, 2013.
Spitzer et al: "Third generation oral contraceptives and risk of venous thromboembolic disorders: an international case-control study. Transnational Research Group on Oral Contraceptives and the Health of Young Women", BMJ, 312(7023), p. 83-88, Jan. 13, 1996.
Vlieg et al: "The venous thrombotic risk of oral contraceptives, effects of oestrogen dose and progestogen type: results of the MEGA case-control study", BMJ, 339:b2921, Aug. 13, 2009.

(56) References Cited

OTHER PUBLICATIONS

WTO: "Venous thromboembolic disease and combined oral contraceptives: results of international multicentre case-control study", Lancet, 346(8990): p. 1575-1582, Dec. 16, 1995.
Office Action dated Jun. 27, 2019 in U.S. Appl. No. 15/737,227 (US 2018-0169022).
Office Action dated May 1, 2019 in U.S. Appl. No. 15/737,233 (US 2018-0185271).
Office Action dated May 17, 2019 in U.S. Appl. No. 15/737,189 (US 2018-0153801).
Office Action dated Nov. 4, 2019 in U.S. Appl. No. 15/737,233 (US 2018-0185271).
Visser et al., "Clinical applications for estetrol," Journal of Steroid Biochemistry and Molecular Biology, 114 (2009) 85-89.
Office Action dated Dec. 2, 2019 in U.S. Appl. No. 15/737,189 (US 2018-0153801).
Visser et al., "Clinical applications for estetrol," Journal of Steroid Biochemistry and Molecular Biology 114 (2009) 85-59.
Office Action dated Dec. 6, 2019, in U.S. Appl. No. 16/573,611 (US 2020-0046729).
Office Action dated Feb. 3, 2020, in U.S. Appl. No. 16/573,611 (US 2020-0046729).
Office Action dated Feb. 6, 2020, in U.S. Appl. No. 15/737,227 (US 2018-0169022).
"Pharmaceutics of Biological Drugs," Editor in chief: Zhao Yingzheng, pp. 17 and 18, Zhejiang University Press (published on Jun. 30, 2011).
"Pharmaceutics," Editor in Chief: Liu Shubao, p. 153, Henan Science and Technology Press (published on Jul. 31, 2007).
Office Action dated Feb. 6, 2020 in Chinese Application No. 201680035627.8.

\* cited by examiner

ORODISPERSIBLE DOSAGE UNIT CONTAINING AN ESTETROL COMPONENT

CROSS-REFERENCE TO RELATED APPLICATIONS

This non-provisional U.S. Patent Application is a Continuation of U.S. application Ser. No. 15/185,337, filed Jun. 17, 2016, which claims priority to European Patent Application No. 15172747.6, filed Jun. 18, 2015, the contents of which are incorporated herein by their entirety by reference.

TECHNICAL FIELD OF THE INVENTION

The present invention provides an orodispersible solid pharmaceutical dosage unit having a weight of 30-1,000 mg and containing at least 0.1 mg of an estetrol component selected from estetrol, estetrol esters and combinations thereof. This solid dosage unit comprises:
- 0.1-25 wt. % of estetrol particles containing at least 80 wt. % of the estetrol component; and
- 75-99.9 wt. % of one or more pharmaceutically acceptable excipients.

The invention also provides a process of preparing the aforementioned solid dosage unit.

Furthermore, the invention relates to the use of the solid dosage unit in medical treatment, female hormone replacement therapy and female contraception, said use comprising sublingual, buccal or sublabial administration of the said dosage unit.

BACKGROUND OF THE INVENTION

Estetrol is a human steroid, produced by the fetal liver during pregnancy only. This natural hormone was discovered in urine of pregnant women by Diczfalusy and coworkers in 1965. Estetrol has the structure of an estrogenic steroid with four hydroxyl groups. Estetrol is synthesized in the fetal liver from estradiol and estriol by the two enzymes 15α- and 16α-hydroxylase. After birth the neonatal liver rapidly loses its capacity to synthesize estetrol because these two enzymes are no longer expressed.

Estetrol reaches the maternal circulation through the placenta and was already detected at nine weeks of pregnancy in maternal urine. During the second trimester of pregnancy high levels were found in maternal plasma, with steadily rising concentrations of unconjugated estetrol to about 1 ng/mL (>3 nmol/L) towards the end of pregnancy. So far the physiological function of estetrol is unknown. The possible use of estetrol as a marker for fetal well-being has been studied quite extensively. However, due to the large intra- and inter-individual variation of maternal estetrol plasma levels during pregnancy this appeared not to be feasible. Since 2001 estetrol has been studied extensively. In humans estetrol was shown to have a high and dose-proportional oral bioavailability and a long terminal elimination half-life of about 28 hours. Results from in vitro studies showed that estetrol binds highly selective to the estrogen receptors with preference for the ERα form of the receptor, unlike the estrogens ethinyl estradiol and 17β-estradiol. Also in contrast with ethinyl estradiol and especially with 17β-estradiol, estetrol does not bind to sex hormone binding globulin (SHBG) and does not stimulate the production of SHBG in vitro.

The properties of estetrol have also been investigated in a series of predictive, well validated pharmacological in vivo rat models. In these models, estetrol exhibited estrogenic effects on the vagina, the uterus (both myometrium and endometrium), body weight, bone mass, bone strength, hot flushes and on ovulation (inhibition). All these effects of estetrol were dose-dependent with maximum effects at comparable dose levels. Surprisingly, estetrol prevented tumour development in a DMBA mammary tumour model to an extent and at a dose level similar to the anti-estrogen tamoxifen and to ovariectomy. This anti-estrogenic effect of estetrol in the presence of 17β-estradiol has also been observed in in vitro studies using human breast cancer cells.

Buccal, sublingual or sublabial administration of estetrol is mentioned in a number of patent applications, including WO 2002/094275, WO 2002/094276, WO 2002/094278 and WO 2003/018026. Estetrol containing dosage units for buccal, sublingual or sublabial administration are not described in these publications.

WO 2010/033832 describes an oral dosage form comprising an estriol compound and a pharmaceutically acceptable matrix material, wherein the oral dosage form releases at least about 90% of the estriol compound in a time of less than about 300 seconds when contacted with saliva of the buccal and/or sublingual cavity.

US 2007/286829 describes an orally administered solid dosage form capable of delivering ethinyl estradiol with improved bioavailability, said solid dosage form comprising (i) about 0.5 μg to about 50 μg of ethinyl estradiol and (ii) an oral dissolution enhancing carrier that provides for at least 15% absorption of the ethinyl estradiol through the oral mucosa when said solid dosage form is orally administered to the patient with 2 ounces of water or less.

U.S. Pat. No. 6,117,446 describes a buccal dosage unit for administering a combination of steroidal active agents, comprising a compressed tablet of a bioerodible polymeric carrier and therapeutically effective amounts of an androgenic agent selected from testosterone and pharmacologically acceptable esters thereof, a progestin and an estrogen. The examples describe buccal dosage units that were prepared by thoroughly mixing the following components: estrogen, progestogen, androgen, polyethylene oxide, carbomer and magnesium stearate. Next, the mixture was granulated by means of fluid bed granulation and the granulate so obtained was pressed into tablets.

Oral dosage units containing estetrol have been described in several patent publications.

WO 2002/094276 describes a pharmaceutical composition for use in a method of hormone replacement therapy, which method comprises administering to a person in need of such a therapy an effective amount of estetrol, said composition containing virtually no progestogen or anti-progestin. WO 2002/094276 describes the preparation of estetrol tablets having a weight of 185 mg, containing 1.5 mg estetrol, on the basis of the following formulation:

|  | mg |
|---|---|
| Estetrol | 1.5 |
| Polyvinylpyrrolidone (Kollidon 25 ® ex BASF) | 12.5 |
| Lactose | 135.795 |
| Microcrystalline cellulose (Avicel PH 101 ®) | 26.25 |
| Glyceryl palmitostearate (Precirol ®) | 2.775 |
| Anhydrous colloidal silica (Aerosil 200 ®) | 1.0 |
| Crospovidone (Polyplasdone XL ®) | 4.0 |
| Coloring agent | 0.18 |

WO 2002/094275 describes the use of an estetrol in a method of increasing libido in a woman, said method comprising administering to said woman an effective amount of estetrol. Oral administration is mentioned as a suitable mode of administration. This patent application describes the same estetrol tablet as WO 2002/094276.

WO 2002/094279 describes the use of estetrol in a method of contraception in mammalian females, which method comprises the oral administration of said estrogenic component and a progestogenic component to a female of childbearing capability in an effective amount to inhibit ovulation. The following formulation for a 185 mg estetrol tablet is described in this international patent application.

|  | mg |
|---|---|
| Estetrol | 1.5 |
| Levonorgestrel | 0.15 |
| Polyvinylpyrrolidone (Kollidon 25 ® ex BASF) | 13.5 |
| Lactose | 135.645 |
| Microcrystalline cellulose (Avicel PH 101 ®) | 26.25 |
| Glyceryl palmitostearate (Precirol ®) | 2.775 |
| Anhydrous colloidal silica (Aerosil 200 ®) | 1.0 |
| Crospovidone (Polyplasdone XL ®) | 4.0 |
| Coloring agent | 0.18 |

WO 2003/041718 describes the use of estetrol in a method of hormone replacement in mammals, which method comprises the oral administration of estetrol and a progestogenic component to a mammal in an effective amount to prevent or treat symptoms of hypoestrogenism. This patent application describes the same estetrol tablet as WO 2002/094279.

WO 2007/081206 describes the use of estetrol in a method of treating an acute vascular disorder in a mammal, said method comprising orally administering to said mammal, upon demand, an effective amount of the estetrol to the mammal. This patent application describes the preparation of hard gelatine capsules, containing 100 mg estetrol and 25 mg sildenafil citrate per capsule. WO 2008/156365 describes the use of estetrol in the treatment of Meconium Aspiration Syndrome (MAS) in a newborn infant, said treatment comprising administering an effective amount of estrogen to said newborn infant within 7 days after birth. The international patent application describes a suppository for use in newborn infants comprising at least 1 μg of estrogen, said suppository further being characterized by a maximum diameter of less than 10 mm and a weight of less than 0.5 g. The excipient contained in the suppository may be based on lipid material that melts at body temperature or it may be based on a hydrophilic component that dissolves or disintegrates when it comes into contact with water.

SUMMARY OF THE INVENTION

The present invention provides an orodispersible solid pharmaceutical dosage unit containing an estetrol component. The dosage unit rapidly releases the estetrol in aqueous environment. The solid dosage unit is easy to manufacture by direct compression and perfectly suited for sublingual, buccal or sublabial administration. Sublingual, buccal and sublabial administration each offer the advantages that the estetrol component does not have to pass through the digestive system and avoids first-pass liver exposure. Furthermore, these modes of administration provide a rapid onset of action.

The solid dosage unit according to the present invention has a weight between 30 and 1,000 mg and contains at least 100 μg of an estetrol component selected from estetrol, estetrol esters and combinations thereof; and comprises:
  0.1-25 wt. % of estetrol particles containing at least 80 wt. % of the estetrol component; and
  75-99.9 wt. % of one or more pharmaceutically acceptable excipients.

This solid dosage is obtainable by a process comprising:
  providing estetrol particles containing at least 80 wt. % of an estetrol component selected from estetrol, estetrol esters and combinations thereof, said estetrol particles having a volume median diameter in the range of 2 μm to 50 μm;
  preparing a dry blend by mixing the estetrol particles with one or more pharmaceutically acceptable excipients; and
  compressing the dry blend into a solid dosage unit.

Rapid and complete dissolution of the estetrol component into saliva is essential for efficient delivery of the component via sublingual, buccal or sublabial administration of the solid dosage unit. The inventors have unexpectedly found that the estetrol component is rapidly released and dispersed into saliva and absorbed through the mucosal lining of the oral cavity if it is present in the solid dosage unit in the form of very small particles.

The invention also provides a process of preparing the aforementioned solid dosage unit, said process comprising the steps of:
  providing estetrol particles containing at least 80 wt. % of an estetrol component selected from estetrol, estetrol esters and combinations thereof, said estetrol particles having a volume median diameter in the range of 2 μm to 50 μm;
  preparing a dry blend by mixing 1 part by weight of the estetrol particles with 2-1,000 parts by weight of one or more pharmaceutically acceptable excipients; and
  compressing the dry blend into a solid dosage unit.

DETAILED DESCRIPTION OF THE INVENTION

Figure 1:
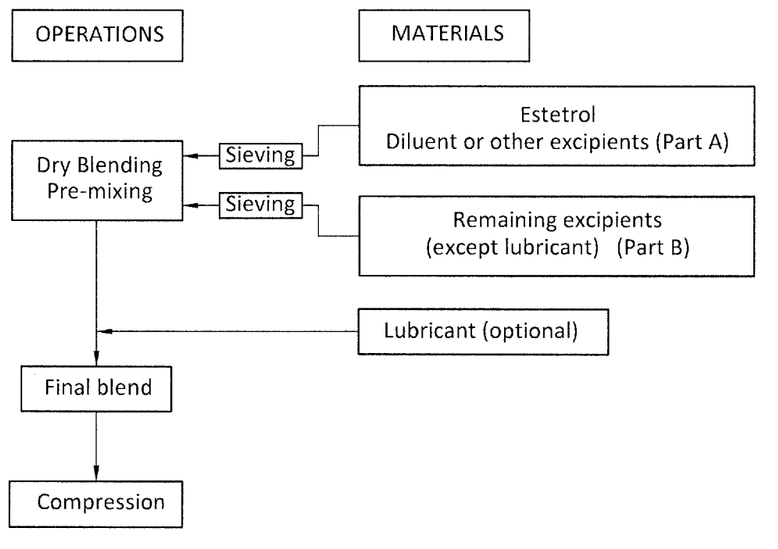
The FIGURE illustrates the manufacturing process flow chart used in Example 3.

A first aspect of the invention relates to an orodispersible solid pharmaceutical dosage unit having a weight between 30 and 1,000 mg, said dosage unit comprising:
  0.1-25 wt. % of estetrol particles containing at least 80 wt. % of an estetrol component selected from estetrol, estetrol esters and combinations thereof; and
  75-99.9 wt. % of one or more pharmaceutically acceptable excipients;
  the solid dosage unit comprising at least 100 μg of the estetrol component; wherein the solid dosage unit can be obtained by a process comprising:
    providing estetrol particles containing at least 80 wt. % of an estetrol component selected from estetrol, estetrol esters and combinations thereof, said estetrol particles having a volume median diameter in the range of 2 μm to 50 μm;
    preparing a dry blend by mixing the estetrol particles with one or more pharmaceutically acceptable excipients; and
    compressing the dry blend into a solid dosage unit.

The term 'estetrol' as used herein refers to 1,3,5 (10)-estratrien-3,15α,16α,17β-tetrol or 15α-hydroxyestriol as well as hydrates of estetrol, e.g. estetrol monohydrate.

The term 'orodispersible dosage unit' as used herein refers to a dosage unit that is designed to rapidly disintegrate in the oral cavity when it comes into contact with saliva and to disperse the estetrol component into the saliva so it may be absorbed through the mucosal lining of the oral cavity.

The term 'sublingual' as used herein refers to the pharmacological route of administration by which the estetrol component diffuses into the blood through tissues under the tongue.

The term 'buccal' as used herein refers to the pharmacological route of administration by which the estetrol component diffuses into the blood through tissues of the buccal vestibule, the area inside the mouth between the lining of cheek (the buccal mucosa) and the teeth/gums.

The term 'sublabial' as used herein refers to the pharmacological route of administration by which the estetrol component is placed between the lip and the gingiva.

Unless indicated otherwise, all percentages mentioned herein are percentages by weight.

Examples of solid dosage units encompassed by the present invention include tablets, dragees, lozenges and films. In accordance with a preferred embodiment, the dosage unit is a tablet, most preferably a compressed tablet.

The solid dosage unit typically has a weight between 40 and 500 mg, more preferably between 50 and 300 mg, and most preferably between 70 and 150 mg.

The solid dosage unit preferably comprises 0.5-25 wt. %, more preferably 1-20 wt. % and most preferably 1.2-15 wt. % of the estetrol component.

The amount of the estetrol component contained in the solid dosage unit preferably lies within the range of 0.3-100 mg, more preferably of 0.5-40 mg and most preferably of 1-20 mg.

The estetrol component of the present invention preferably is selected from the group consisting of estetrol, esters of estetrol wherein the hydrogen atom of at least one of the hydroxyl groups has been substituted by an acyl radical of a hydrocarbon carboxylic, sulfonic acid or sulfamic acid of 1-25 carbon atoms; and combinations thereof. Even more preferably, the estetrol component is estetrol (including estetrol hydrates). Most preferably, the estetrol component contained in the dosage unit is estetrol monohydrate.

The particle size of the estetrol particles in the solid dosage unit should be adequate for achieving sufficient absorption of the estetrol component after sublingual, buccal or sublabial administration. The estetrol particles within the solid dosage unit and (independently) the estetrol particles used in the preparation of the solid dosage unit preferably have a volume median diameter in the range of 3 µm to 35 µm, more preferably in the range of 4 µm to 25 µm and most preferably in the range of 5 µm to 15 µm.

The estetrol particles within the solid dosage unit and (independently) the estetrol particles used in the preparation of the solid dosage unit preferably contain not more than a limited amount of particles with a particle size in excess of 60 µm. Preferably, not more than 10 vol. % of more than 60 µm ($D_{90}$), more preferably not more than 5 vol. % of the estetrol particles have a particle size of more than 60 µm ($D_{95}$). Even more preferably, not more than 10 vol. % of more than 40 µm ($D_{90}$), more preferably not more than 5 vol. % of the estetrol particles have a particle size of more than 40 µm ($D_{95}$).

The particles size distribution of the estetrol particles, and of other particulate materials used in the present process, may suitably be determined by means of laser diffraction. The particle size distribution of the estetrol particles within the solid dosage unit can suitably be determined using spectroscopic techniques, e.g. Raman mapping.

The solid dosage unit of the present invention offers the advantage that the estetrol component is rapidly released when the dosage unit is introduced into the oral cavity and comes into contact with saliva. The rate of release of the estetrol component from the dosage unit can suitably be determined using the dissolution test described in the Examples, or a disintegration test according to Ph. Eur. 2.9.1 ("Disintegration of tablets and capsules") and USP <701> ("Disintegration"), also described in the Examples. The solid dosage unit of the present invention, when subjected to the aforementioned dissolution test, typically releases at least 50%, more preferably at least 70% and most preferably at least 80% of the estetrol component after 5 minutes. The solid dosage unit of the present invention, when subjected to the aforementioned disintegration test, typically disintegrates within less than 5 minutes, more preferably within less than 2 minutes, still more preferably within less than 1.5 minutes, still more preferably within less than 1 minute, still more preferably within less than 45 seconds, and most preferably within less than 30 seconds.

The estetrol particles employed in the solid dosage unit and in the present process preferably contain at least 90 wt. % of the estetrol component, more preferably at least 95 wt. % of the estetrol component and most preferably at least 99 wt. % of the estetrol component. Besides the estetrol component, the estetrol particles can suitably contain pharmaceutically acceptable ingredients that aid dispersion of the dosage unit and dissolution and absorption of the estetrol component. Examples of such ingredients include microcrystalline cellulose, tensioactive agents, cosolvents, absorption enhancer, superdisintegrants and buffering agents.

The estetrol particles typically represent between 0.5-35 wt. % of the dosage unit. More preferably, the estetrol particles represent 1-22 wt. %, most preferably 1.2-15 wt. % of the dosage unit.

The dosage unit of the present invention preferably contains 50-99.5 wt. %, more preferably 55-90 wt. % and most preferably 60-88 wt. % of filler selected from maltose, fructose, sucrose, lactose, glucose, galactose, trehalose, xylitol, sorbitol, erythritol, maltitol, mannitol, isomalt, microcrystalline cellulose, calcium salts (e.g. calcium phosphates) and combinations thereof.

According to a particularly preferred embodiment, the dosage unit contains 30-99.5 wt. %, more preferably 50-90 wt. % and most preferably 60-80 wt. % of filler selected from lactose, xylitol, sorbitol, erythritol, mannitol, microcrystalline cellulose and combinations thereof.

Advantageously, the dosage unit contains at least 20 wt. % of sugar alcohol selected from mannitol, xylitol and combinations thereof. More preferably, the dosage unit contains 30-90 wt. % of sugar alcohol selected from mannitol, xylitol and combinations therof Most preferably, the dosage unit contains 40-80 wt. % of sugar alcohol selected from mannitol, xylitol and combinations thereof.

Dosage unit according to any one of the preceding claims, wherein the dosage unit contains 0.1-20 wt. %, more preferably 0.2-10 wt. % and most preferably 1-5 wt. % of a disintegrating agent selected from modified starches (e.g. sodium salt of carboxymethyl starch), crosslinked polyvinyl pyrrolidone, crosslinked carmellose and combinations thereof.

The combination of estetrol particles, filler and disintegrating agent typically constitutes at least 70 wt. % of the solid dosage unit. More preferably, said combination constitutes at least 80 wt. % and most preferably at least 90 wt. % of the dosage unit.

The solid dosage unit of the present invention preferably contains 0-60 wt. %, more preferably 5-40 wt. % and most preferably 10-35 wt. % microcrystalline cellulose.

According to another preferred embodiment, the dosage unit contains 0.1-2 wt. %, more preferably 0.2-1.5 wt. % and most preferably 0.5-1 wt. % of lubricant selected from sodium stearyl fumarate, magnesium stearate, stearic acid, sodium lauryl sulfate, talc, polyethylene glycol, calcium stearate and mixtures thereof.

Other excipients that may suitably be incorporated in the dosage include mucoadhesive agents, flavouring, colouring, sweeteners (other than sweet tasting fillers), glidents and combinations thereof.

The solid dosage unit may contain one or more other pharmaceutically active ingredients besides the estetrol component. Examples of such other pharmaceutically active ingredients include steroid hormones. The solid dosage unit of the present invention preferably contains 0.05-10 mg, more preferably 0.1-5 mg of one or more progestogens, preferably one or more progestogens selected from progesterone, levonorgestrel, norgestimate, norethisterone, norethisteron-acetate (NETA), dydrogesterone, drospirenone, 3-beta-hydroxydesogestrel, 3-keto desogestrel (=etonogestrel), 17-deacetyl norgestimate, 19-norprogesterone, acetoxypregnenolone, allylestrenol, anagestone, chlormadinone, cyproterone, demegestone, desogestrel, dienogest, dihydrogesterone, dimethisterone, ethisterone, ethynodiol diacetate, flurogestone acetate, gastrinon, gestodene, gestrinone, hydroxymethylprogesterone, hydroxyprogesterone, lynestrenol (=lynoestrenol), medrogestone, medroxyprogesterone, megestrol, melengestrol, nestorone, nomegestrol, nomegestrol-acetate (NOMAC), norethindrone (=norethisterone), norethynodrel, norgestrel (includes d-norgestrel and dl-norgestrel), norgestrienone, normethisterone, progesterone, quingestanol, (17alpha)-17-hydroxy-11-methylene-19-norpregna-4,15-diene-20-yn-3-one, tibolone, trimegestone, algestone acetophenide, nestorone, promegestone, 17-hydroxyprogesterone esters, 19-nor-17hydroxyprogesterone, 17alpha-ethinyl-testosterone, 17alpha-ethinyl-19-nor-testosterone, d-17beta-acetoxy-13beta-ethyl-17alpha-ethinyl-gon-4-en-3-one oxime and prodrugs of these compounds. Preferably the one or more progestogens used in accordance with the present invention is selected from the group consisting of progesterone, desogestrel, etonogestrel, gestodene, dienogest, levonorgestrel, norgestimate, norethisterone, norethisteron-acetate (NETA), nomegestrol, nomegestrol-acetate (NOMAC), drospirenone, trimegestone, nestorone and dydrogesterone.

The solid dosage unit according to the present invention preferably contains 0.05-100 mg, more preferably 0.1-50 mg of one or more androgens, preferably one or more androgens selected from testosterone, dehydroepiandrosterone (DHEA); DHEA-sulphate (DHEAS); testosterone esters (e.g. testosterone undecanoate, testosterone propionate, testosterone phenylpropionate, testosterone isohexanoate, testosterone enantate, testosterone bucanate, testosterone decanoate, testosterone buciclate); methyltestosterone; mesterolon; stanozolol; androstenedione; dihydrotestosterone; androstanediol; metenolon; fluoxymesterone; oxymesterone; methandrostenolol; MENT and prodrugs of these compounds. Most preferably the one or more androgens are selected from the group consisting of testosterone, DHEA and MENT.

Another aspect of the present invention relates to the use of the aforementioned solid dosage unit in medical treatment, in female hormone replacement therapy or in female contraception, said use comprising sublingual, buccal or sublabial administration of the dosage unit. Examples of medical treatment in which the solid dosage unit of the present invention may suitably be used include treatment of osteoporosis and estrogen add-back treatment in endometriosis, breast cancer or prostate cancer. In accordance with a preferred embodiment, the solid dosage unit is used in female hormone replacement therapy or female contraception. Most preferably, the solid dosage is used in female hormone replacement therapy, especially to treat vulvovaginal atrophy and/or vasomotor symptoms.

The use of the solid dosage unit in medical treatment, in female hormone replacement therapy or in female contraception, typically comprises sublingual, buccal or sublabial administration of the dosage unit to provide at least 0.1 mg, more preferably 0.5-100 mg and most preferably 1-40 mg of the estetrol component.

To treat vulvovaginal atrophy the dosage unit is preferably administered in an amount sufficient to provide at least 0.1 mg of the estetrol component. More preferably, the administered dosage unit provides at least 0.5 mg, most preferably at least 1 mg of the estetrol component. In the treatment of vulvovaginal atrophy the dosage unit is preferably administered in an amount that provides no more than 50 mg, more preferably not more than 20 mg and most preferably not more than 10 mg of the estetrol component.

To treat vasomotor symptoms the dosage unit is preferably administered in an amount sufficient to provide at least 0.2 mg of the estetrol component. More preferably, the administered dosage unit provides at least 1 mg, most preferably of at least 2 mg of the estetrol component. In the treatment of vasomotor symptoms the dosage unit is preferably administered in an amount that provides no more than 100 mg, more preferably not more than 40 mg and most preferably not more than 20 mg of the estetrol component.

Typically, these uses of the solid dosage unit comprise once daily administration of the dosage unit during a period of at least 1 week, more preferably of at least 2 weeks. During these periods the solid dosage unit is preferably administered to provide a daily dose of at least 0.05 mg, more preferably of 0.1-40 mg and most preferably of 0.2-20 mg of the estetrol component.

To treat vulvovaginal atrophy the dosage unit is preferably administered to provide a daily dose of at least 0.1 mg of the estetrol component. More preferably, the dosage unit is administered to provide a daily dose of 0.5-20 mg, most preferably of 1-10 mg of the estetrol component. To treat vasomotor symptoms the dosage unit is preferably administered to provide a daily dose of at least 0.2 mg of the estetrol component. More preferably, the dosage unit is administered to provide a daily dose of 1-40 mg, most preferably 2-20 mg of the estetrol component.

Yet another aspect of the invention relates to a process of preparing a solid dosage unit as described herein before, said process comprising the steps of:
  providing estetrol particles containing at least 80 wt. % of an estetrol component selected from estetrol, estetrol esters and combinations thereof, said estetrol particles having a volume median diameter in the range of 2 μm to 50 μm;
  preparing a dry blend by mixing 1 part by weight of the estetrol particles with 2-1,000 parts by weight of one or more pharmaceutically acceptable excipients; and
  compressing the dry blend into a solid dosage unit.

The process of the present process preferably does not comprise addition of liquid solvent during or after the combining of the estetrol particles and the one or more pharmaceutically acceptable excipients.

In the present process the dry blend that is compressed into a solid dosage unit is preferably produced by combining the estetrol particles with the one or more pharmaceutically acceptable excipients in a weight ratio that is in the range of 1:3 to 1:500, more preferably in the range of 1:4 to 1:100 and most preferably in the range of 1:5 to 1:10.

The dry blend that is compressed into the solid dosage unit preferably contains 50-99.5 wt. %, more preferably 55-90 wt. % and most preferably 60-88 wt. % of filler as defined herein before.

According to a particularly preferred embodiment the dry blend contains 30-99.5 wt. %, more preferably 50-90 wt. % and most preferably 60-80 wt. % of filler selected from lactose, xylitol, sorbitol, erythritol, mannitol, microcrystalline cellulose and combinations thereof.

Sugar alcohol selected from mannitol, xylitol and combinations thereof is advantageously contained in the dry blend in a concentration of at least 20 wt. %. More preferably, said sugar alcohol is contained in the dry blend in a concentration of 30-90 wt. %, most preferably of 40-80 wt. %.

According to another preferred embodiment, the dry blend contains 0.1-20 wt. %, more preferably 0.2-10 wt. % and most preferably 1-5 wt. % of a disintegrating agent selected from modified starches, croslinked polyvinylpyrrolidone, crosslinked carmellose and combinations thereof.

The combination of estetrol particles, filler and disintegrating agent typically constitutes at least 70 wt. % of the dry blend. More preferably, said combination constitutes at least 80 wt. % and most preferably at least 90 wt. % of the dry blend.

The solid dosage unit of the present invention preferably contains 0-60 wt. %, more preferably 5-40 wt. % and most preferably 10-35 wt. % microcrystalline cellulose.

The dry blend employed in the present process preferably contains 0-60 wt. %, more preferably 5-40 wt. % and most preferably 10-35 wt. % microcrystalline cellulose.

The dry blend that is compressed into the solid dosage unit preferably contains 0.1-2 wt. %, more preferably 0.2-1.5 wt. % and most preferably 0.5-1 wt. % of lubricant selected from sodium stearyl fumarate, magnesium stearate, stearic acid, sodium lauryl sulfate, talc, polyethylene glycol, calcium stearate and mixtures thereof.

The dry blend is preferably compressed into a solid dosage unit by means of direct compression.

The solid dosage units obtained by the present method can be packaged in different ways.

Preferably, the dosage units are packaged in a blister pack containing at least 14 dosage units.

The invention is further illustrated by means of the following non-limiting examples.

EXAMPLES

Dissolution Test

The dissolution test described below can be used to study the dissolution behaviour of orodispersible dosage units.

Dissolution Apparatus

Paddle and basket dissolution tester VanKel VK 7010 or VK 7025, autosampler VK 8000, 1000 mL dissolution vessels and porous micron filters (35 pin)

Dissolution Medium

Transfer 9,000 ml of demineralised water into a volumetric flask of 10,000 ml.

Add 68.05 g of $KH_2PO_4$ and 8.96 g NaOH and stir the solution until everything is dissolved.

Mix the solution and adjust the pH to 6.8 with NaOH or phosphoric acid, if necessary and make up to volume with demineralised water.

Dissolution Procedure

Transfer 900 ml of Dissolution Medium into each vessel of the paddle apparatus.

Assemble the apparatus, warm the medium to 37±0.5° C., and remove the thermometer.

Place in each of the six vessels one tablet at the bottom before starting the rotation of the paddles.

Start the rotation of the paddles immediately.

Use a stirring speed of 50 rpm.

Take samples of 5 ml from the dissolution vessels after 5, 10, 20, 30, 45, 60, 75 and 90 minutes for a complete dissolution profile. Take the sample from a position midway between the surface of the dissolution medium and the top of the paddle blade and not less than 10 mm from the vessel wall. The removed dissolution volume is not replaced by fresh dissolution medium.

Estetrol concentrations in the samples were determined by means of HPLC using estetrol stock solutions as a reference.

Preparation of Mobile Phase (MP) Phosphate Buffer

Transfer 1.15 g of $NH_4H_2PO_4$ (10 mM) into a 1,000 ml of demineralised water, dissolve it and adjust the pH to 3.0 with phosphoric acid.

HPLC Apparatus

Alliance 2695 Separations module consisting of a quaternary solvent delivery system, a variable volume injector, a temperature controlled autosampler, column thermostat and Photodiode array detector 2996 (all by Waters)

Analytical column: Symmetry C18, 3.9×150 mm, dp=5 µm (ex Waters)

Guard column: Security guard columg C18, 4×3 mm (Phenomenex)

Flow: 1.0 mL/min

Detection: UV @ 280 nm

Column temperature: 30° C.

Autosampler temperature: 10° C.

Injection volume: 100 µL

Run time: 12 min

Elution Gradient

| Time (min) | Acetonitrile (%) | Phosphate buffer (%) |
|---|---|---|
| 0 | 20 | 80 |
| 9 | 75 | 25 |
| 10 | 20 | 80 |
| 12 | 20 | 80 |

The dissolution tests are conducted in triplicate.

Particle Size Measurements

Particle size distribution of estetrol monohydrate is performed using a MALVERN MASTERS IZER MICROPLUS laser particle size analyzer.

Preparation of Dispersion Medium

Weigh 1 g of estetrol monohydrate and 1 g of sorbitan trioleate into a flask.
Add 1 litre of n-hexane and mix for at least 1 hour at room temperature
Filter through a 0.45 µm filter.

Sample Preparation

Put 100 mg of sample in a 25 mL beaker.
Add some drops of dispersion medium.
Mix carefully with a glass rod to suspend well the powder.
Add 10 mL of dispersion medium.
Perform the analysis with the sample dispersion unit's speed at 3000-3500 rpm.

Analysis

Particle size measurements are performed three times using the same dispersion. The final result is obtained by averaging the results of the three determinations.

Example 1

A sublingual tablet is prepared by means of the procedure described below.
A tabletting mixture having the composition shown in Table 1 is prepared by dry blending, using a low shear mixer.

TABLE 1

| Ingredients | Wt. % |
|---|---|
| Milled estetrol [1] | 12.5 |
| Mannitol | 47.5 |
| Lactose | 30 |
| PVP (polyvinylpyrrolidone) | 4 |
| Sodium crosscarmellose | 4 |
| Flavour | 0.5 |
| Aspartame | 1 |
| Magnesium stearate | 0.5 |

[1] $D_{(v;0.5)} = 15$ µm

The tabletting mixture is compressed into 80 mg round tablets with a diameter of 6.5 mm. The estetrol content of these tablets is 10 mg.

Example 2

A sublingual tablet is prepared by means of the procedure described below.
A tabletting mixture having the composition shown in Table 2 is prepared by dry blending using a low shear mixer.

TABLE 2

| Ingredients | Wt. % |
|---|---|
| Milled estetrol [1] | 12.5 |
| Mannitol | 37.5 |
| Xylitol | 10 |
| Microcrystalline cellulose | 33 |
| Sodium starch glycolate | 5 |
| Flavour | 0.5 |
| Aspartame | 1 |
| Magnesium stearate | 0.5 |

[1] $D_{(v;0.5)} = 15$ µm

The tabletting mixture is compressed into 80 mg round tablets with a diameter of 6.5 mm. The estetrol content of these tablets is 10 mg.

Example 3

Five different sets of sublingual tablets (formulations A to E) were prepared by means of the procedure described below and illustrated in the FIGURE.

The target amounts of estetrol per tablet were as follows: 100 µg for formulation A, 1 mg for formulation B, and 10 mg for formulations C, D and E.

The target weights for the tablets were as follows: 30 mg for formulation A, 1000 mg for formulation B, and 80 mg for formulations C, D and E.

The estetrol was mixed with a part of the main diluent and screened over a 800 µm screen. All other excipients were also screened over a 800 µm screen.

The materials were weighed and transferred into the mixing container (except for magnesium stearate) and mixed for 15 minutes. Finally, magnesium stearate was added and mixed for a further 3 minutes.

Compression was executed using a single punch machine equipped with a proper punch (5 mm punch for 30 mg tablets (A), 6 mm for 80 mg tablets (C, D and E) and 15 mm for 1000 mg tablets (B)).

Disintegration time was quantified according to the known protocol described in Ph. Eur. 2.9.1 ("Disintegration of tablets and capsules"), and in USP <701> ("Disintegration") using water as the specified liquid.

Hardness was measured using the known protocol described in Ph. Eur. 2.9.8 ("Resistance to crushing of tablets").

The final formulations and corresponding tablet results can be found in Tables 3 and 4 below.

All formulations were prepared and processed into tablets without encountering any specific difficulties. It should be noted that a good flowing diluent was used in all formulations to overcome flowability issues and that the concentration of magnesium stearate was at least 1.5% to avoid sticking.

TABLE 3 details of the formulations in Wt. %

| Formulation # | A | B | C | D | E |
|---|---|---|---|---|---|
| Milled Estetrol [1] | 0.33 | 0.1 | 12.50 | 12.40 | 12.35 |
| Mannitol | 83.14 | 83.47 | 71.00 | 48.47 | 38.62 |
| Maize starch | 10.01 | 10.00 | 10.00 | | |
| Crospovidone | 5.01 | 5.01 | 4.99 | | |
| Lactose | | | | 29.68 | |
| PVP (polyvinylpyrrolidone) | | | | 3.98 | |
| Sodium crosscarmellose | | | | 3.98 | |
| Xylitol DC | | | | | 9.91 |
| Microcrystalline cellulose | | | | | 32.66 |
| Sodium starch glycolate | | | | | 4.97 |
| Magnesium stearate | 1.51 | 1.51 | 1.50 | 1.49 | 1.48 |

[1] $D_{(v;0.5)}$ = 15 μm

TABLE 4 experimentally determined characteristics of the Tablets

| Test (average result of 6 samples) Formulation # | Disintegration time (min:sec) | Hardness (N) | Weight (mg) |
|---|---|---|---|
| A | 0:53 | 39.57 | 33.22 |
| B | 1:07 | 86.07 | 1060.37 |
| C | 0:39 | 57.49 | 81.16 |
| D | 0:39 | 42.71 | 78.48 |
| E | 0:38 | 37.29 | 76.49 |

It can be seen that all tablets were obtained with a final weight close to their target weight and that the disintegration times, even for the largest 1 g tablet, were very short, in accordance with the intended sublingual, buccal or sublabial administration route for these tablets. Finally, the hardness of all tablets was within a very acceptable range.

Example 4

A randomized, open-label, two-period, cross-over, pharmacokinetic study is conducted to compare sublingual bioavailability of 10 mg estetrol administered in one 100 mg tablet with oral availability of estetrol contained in a 83 mg tablet containing 10 mg estetrol. These tablets are administered sublingually and orally to healthy female volunteers under fasting conditions.

Ten healthy female subjects are selected on the basis of the following criteria: age of 45-65 years (inclusive), non-smokers or past smokers (at least 6 months before dosing), body-mass index (BMI)=18.5 to 30 kg/m² (inclusive at the time of the screening).

The composition of the 100 mg sublingual tablets is described in Table 5 below.

TABLE 5

| | Quantity (Wt. %) | Function |
|---|---|---|
| Milled Estetrol [1] | 10 | Active ingredient |
| Ludiflash ® [2] | 84 | Diluent/binder/super disintegrant |
| Kollidon CL-SF ® [3] | 3 | Super disintegrant |
| Magnesium stearate | 3 | Lubricant |

[1] $D_{(v;0.5)}$ = 15 μm
[2] A mixture of mannitol (90 wt. %), Kollidon CL-SF ® [3] (5 wt. %) and Kollicoat ® SR30D (a polyvinyl acetate dispersion in povidone) (5 wt. %)
[3] crospovidone superfine grade These tablets have a very fast disintegration time (of 40 seconds on average).

At the start of the first and the second period of the study, between 07:00 am and 07:28 am, 5 subjects receive a single dose of the sublingual formulation of estetrol by administering one estetrol tablet (tablet weight 100 mg; 10 mg estetrol) and 5 subjects receive a single oral dose of the oral estetrol formulation by administering one estetrol tablet (tablet weight 83 mg; 10 mg estetrol), ingested together with 200 ml water.

Subjects are required to fast for at least 10 hours prior to tablet administration and for at least 4 hours after administration. Drinking of water or beverages is not permitted within 1 hour before the drug administration. Subjects receive 200 ml of water 1 hour prior to and 2 hours after tablet administration. Subjects are free to drink water and fruit tea from 4 hours following the tablet administration. Standardized meals are provided 10.5 hours before and 4, 6, 9, and 13 hours after tablet administration.

The sequence of events that occurs during the first and second period is shown in Table 6:

TABLE 6

| | Event |
|---|---|
| First period | |
| Day 1 | Confinement from 19:00 |
| Day 2 | Dosing, blood and urine sampling, confinement |
| Day 3 | Exit procedure, confinement till 8 am |
| Days 4-8 | Return visits |
| Days 9-13 | Wash out |
| Second period | |
| Day 14 | Confinement from 19:00 |
| Day 15 | Dosing, blood and urine sampling, confinement |
| Day 16 | Exit procedure, confinement till 8 am |
| Days 17-21 | Return visits |
| Days 22-26 | Wash out |
| Day 27 | Administration of a progestin |
| Day 28 | Phone call, progestin withdrawal test check |

The blood and urine sampling schedule used in this study is shown in Table 7.

TABLE 7

| | |
|---|---|
| Blood sampling | Blood collection (4 ml) is performed prior to administration of the tablet (0), and subsequently 0:10, 0:15, 0:20, 0:25, 0:30, 0:35, 0:40, 0:45, 0:50, 0:55, 1:00, 1:10, 1:20, 1:30, 2, 3, 4, 6, 10, 16, 24, 48, 72, 96, 120, 144 hours after administration. Total number of blood collections in each period is 27. |
| Urine sampling | Urine collection is performed prior to administration of the tablet and 2, 4, 8, 12, 24, 48, 72, 96, 120 and 144 hours after administration. Total number of urine collections in each period is 11. |

The estetrol concentration in the collected blood samples is determined by means of HPLC/MS/MS. The concentrations of glucuronided estetrol (D-ring) in the urine samples is also determined with the help of HPLC/MS/MS.

Results of these analyses show that the bioavailability of sublingually administered estetrol is comparable or even superior to orally administered estetrol. Furthermore, the data suggest that sublingually administered estetrol has an earlier bioavailability compared to orally administered estetrol. Sublingual estetrol has less impact on a liver function parameter.

The invention claimed is:

1. A process of preparing an estetrol orodispersible solid pharmaceutical dosage unit having a weight between 30 and 1,000 mg, the dosage unit comprising:
   (a) 0.1-25 wt. % of estetrol particles containing at least 80 wt. % of an estetrol component selected from estetrol, estetrol esters, and combinations thereof; and
   (b) 75-99.9 wt. % of one or more pharmaceutically acceptable excipients;
   wherein the solid dosage unit contains at least 100 µg of the estetrol component and disintegrates within less than 5 minutes when subjected to disintegration testing in accordance with USP <701>("Disintegration") using water as the disintegration medium, the process comprising:
   (i) providing estetrol particles having a volume median diameter between 2 µm to 50 µm and containing at least 80 wt. % of an estetrol component selected from estetrol, estetrol esters and combinations thereof;
   (ii) mixing 1 part by weight of the estetrol particles with 2-1,000 parts by weight of one or more pharmaceutically acceptable excipients to obtain a dry blend; and
   (iii) compressing the dry blend into a solid dosage unit.

2. The process according to claim 1, wherein the process does not comprise addition of liquid solvent during or after the combining of the estetrol particles and the one or more pharmaceutically acceptable excipients.

3. The process according to claim 1, wherein the solid dosage unit is formed by direct compression.

4. The process according to claim 1, wherein the dosage unit has a weight between 40 and 500 mg.

5. The process according to claim 1, wherein the dosage unit contains 0.5-25 wt. % of the estetrol component.

6. The process according to claim 1, wherein the dosage unit contains 0.3-100 mg of the estetrol component.

7. The process according to claim 1, wherein the estetrol component is estetrol.

8. The process according to claim 1, wherein the estetrol particles have a volume median diameter of 3-35 µm.

9. The process according to claim 1, wherein the dosage unit contains 50-99.5 wt. % of filler selected from maltose, fructose, sucrose, lactose, glucose, galactose, trehalose, xylitol, sorbitol, erythritol, maltitol, mannitol, isomalt, microcrystalline cellulose, calcium salts, and combinations of any thereof.

10. The process according to claim 1, wherein the dosage unit contains 30-99.5 wt. % of filler selected from lactose, xylitol, sorbitol, erythritol, mannitol, microcrystalline cellulose, and combinations of any thereof.

11. The process according to claim 1, wherein the dosage unit contains 30-90 wt. % of sugar alcohol selected from mannitol, xylitol, and combinations thereof.

12. The process according to claim 1, wherein the dosage unit contains 0.1-20 wt. % of a disintegrating agent selected from modified starches, crosslinked polyvinyl pyrrolidone, crosslinked carmellose, and combinations of any thereof.

13. The process according to claim 1, wherein the dosage unit contains 5-40 wt. % of microcrystalline cellulose.

14. The process according to claim 1, wherein the dosage unit contains 0.1-2 wt. % of lubricant selected from sodium stearyl fumarate, magnesium stearate, stearic acid, sodium lauryl sulfate, talc, polyethylene glycol, calcium stearate, and combinations of any thereof.

* * * * *